United States Patent
Sorell Gómez et al.

(10) Patent No.: US 6,905,835 B2
(45) Date of Patent: Jun. 14, 2005

(54) ASSAY FOR ANTI TRANSGLUTAMINASE ANTIBODIES DETECTION USEFUL IN CELICAC DISEASE DIAGNOSIS

(75) Inventors: Luis Tomás Sorell Gómez, C. Habana (CU); Boris Ernesto Acevedo Castro, C. Habana (CU)

(73) Assignee: Centro De Ingenieria Genetica Y Biotecnologia CIGB, Habana (CU)

( * ) Notice: Subject to any disclaimer, the term of this patent is extended or adjusted under 35 U.S.C. 154(b) by 390 days.

(21) Appl. No.: 09/866,232

(22) Filed: May 25, 2001

(65) Prior Publication Data

US 2002/0006633 A1 Jan. 17, 2002

(30) Foreign Application Priority Data

Jun. 7, 2000 (CU) .......................................... 2000-0132

(51) Int. Cl.$^7$ ............................................... G01N 33/53
(52) U.S. Cl. .......................... 435/7.92; 435/7.1; 435/4; 435/7.93; 435/7.94; 435/7.95; 435/970; 435/971; 436/513; 436/514; 436/518; 436/810
(58) Field of Search ................... 435/7.1, 4, 7.92–7.95, 435/970, 971; 436/513, 514, 518, 810

(56) References Cited

U.S. PATENT DOCUMENTS 4,012,494 A * 3/1977 Ling .......................... 436/518

6,319,726 B1 * 11/2001 Schuppan et al. .......... 436/506
2001/0036639 A1 * 11/2001 Fine ........................... 435/7.1

FOREIGN PATENT DOCUMENTS

WO    WO 0129090    * 4/2001

* cited by examiner

Primary Examiner—Bao-Thuy L. Nguyen
(74) Attorney, Agent, or Firm—Hoffmann & Baron, LLP

(57) ABSTRACT

A non-instrumental assay for the diagnosis of celiac disease based on the general immunochromatographic assay principles. The assay is rapid and simple and allows the reliable detection of anti transglutaminase antibodies, of both IgA and IgG isotype, in samples of human serum, plasma or blood, using as tracer the antigen transglutaminase conjugated to a colored substance, like colloidal gold or colored latex particles. The conjugated antigen is deposited onto an inert fibrous support, from where it can be released by a liquid sample. The antibodies in the sample react with the conjugated antigen developing an immunocomplex that migrates through a carrier membrane, like nitrocellulose or nylon with a pore size that allows a laminar flow of the reagents, until it reacts with the same antigen transglutaminase immobilized onto a reactive zone of the membrane. As a consequence of this reaction the immunocomplex will be trapped in the reaction site and a colored signal will be seen. Therefore a visually detectable signal in the reactive zone of the membrane indicates a positive result for the detection of anti transglutaminase antibodies in the sample.

6 Claims, 3 Drawing Sheets

Positive sample

Negative sample

AFTER 15 MINUTES

ASSAY FOR ANTI TRANSGLUTAMINASE ANTIBODIES DETECTION USEFUL IN CELICAC DISEASE DIAGNOSIS

The present invention is related with the field of biotechnological, particularly with biomedical diagnosis. The technical objective of the invention is to develop a rapid, simple, and reliable one-step visual assay for the detection of anti transglutaminase antibodies, of both IgA and IgG isotypes, in samples of human serum, plasma or blood. Until now the detection of anti transglutaminase antibodies have been performed by instrumental methods like enzyme linked immunosorbent assay (ELISA) or by radioligand assay (RLA). These assays have shown to be useful for celiac disease diagnosis.

Celiac disease (CD) is a severe gastrointestinal disease that affects genetically susceptible individuals. CD is characterized by a permanent intolerance of proteins from wheat, barley, rye, and oats. Although the physiopatholgy of CD is not completely understood it is clear that the presence of the toxic proteins in the patient's diet causes a total or partial damage of intestinal mucosa (Brandtzaeg, P. 1997. Mechanisms of gastrointestinal reactions to food. Environmental Toxicology and Pharmacology 4;9–24) leading to severe malabsorption syndromes and causing diarrhea, vomit, abdominal pain, anorexia, growth retard, under nutrition and anemia. CD has been associated with a higher risk for intestinal cancer in non-diagnosed and untreated patients (Holmes GKT, 1989. Malignancy in coeliac disease-effect of a gluten-free diet, Gut 30;333–338). CD affects mainly children under three years old, but it is also common in adults, and sometimes is clinically atypical or asymptomatic (Ferguson A, et al. 1992. Definitions and diagnostic criteria of latent and potential coeliac disease. Ed by Aurricchio S, Visakorpi J K, in Epidemiology of CD. Dyn Nutr Res, Basel, Karger 2;119–127). CD is more frequent in patients with other genetic or autoimmune disease, as insulin dependent diabetes mellitus, Down syndrome, selective IgA deficiency, and dermatitis herpetiformis. (Sirgus N et al. 1993. Prevalence of coeliac disease in diabetic children and adolescents in Sweden. Acta Pediatr 66;491–494; Zubillaga P et al. 1993. Down syndrome and coeliac disease. J Pediatr Gastroenterol Nutr 16:168–171; Boyce N 1997. Testing for celiac disease may be soon on the rise. LabMedica Internat 14(4):8)

The clinical symptoms CD could be confused with those produced by other gastrointestinal diseases. In these cases CD is misdiagnosed and patients do not receive the specific treatment, that is, a complete elimination of gluten in their diet. On the other hand, if a non-celiac patient is wrongly diagnosed as celiac, he would undergo on unnecessary gluten free diet for his whole life. That's why a precise diagnosis of CD is essential. Currently the gold standard for CD diagnosis is intestinal biopsy, repeated three times:

at the onset of the clinical symptoms.

after several months on a gluten free diet.

after a challenge with gluten

Because intestinal biopsy is an invasive method and precise serological test have been developed, the above criteria has been revised (Walker-Smith et al. 1990. Revised criteria for diagnosis of coeliac disease. Report of Working group of European Society of Pediatric Gastroenterology and Nutrition. Arch Dis Child 65:909–911). Nowadays serological tests can be done at the onset of clinical symptoms and when they are positive, a confirmatory intestinal biopsy will be indicated. The response to the treatment with a gluten-free diet can be also followed by serological tests. If discrepancies occur between the clinical response to the treatment and the result of serological tests a second intestinal biopsy should be indicated. Several serological tests have been developed for celiac disease diagnosis, as the detection of antibodies to cellular antigens, or antibodies to food antigens, like gliadins. There are diagnostic kits for the detection of:

Anti-endomysial antibodies

Anti-reticulin antibodies

Anti-gliadin antibodies

Anti-endomysial antibodies (EMA) have shown to be the most specific one for the serological diagnosis of CD (Kapuschinska A et al. 1987. Disease specificity and dynamics of changes in IgA class anti-endomysial antibodies in celiac disease. J Pediatric Gastroenterol 6:529–534; Rossi T M et al. 1988. Relationship of endomysial antibodies to jejunal mucosal pathology: specificity towards both symptomatic and asymtomatic celiac. J Pediatr Gastroenterol Nutr 7:858–863). Anti-endomysial antibodies are detected by indirect immunofluorescence (IF) using slides of monkey endomysium or human umbilical cord, which are incubated with the serum samples. The assay requires high technical expertise to perform the test and for a correct interpretation of the results due to its intrinsic subjectivity. But EMA is not a good method for the analysis of large number of samples in the screening of CD in risk groups because of its complexity and high costs. Another disadvantage is that it only detects anti-endomysial antibodies of IgA isotype and it is known that some CD patients have a selective deficit of IgA. These patients will be negative by the test.

On the other hand anti-gliadin antibodies (AGA) have also been extensively used for serological diagnosis of CD (Stern M et al. 1996. Validation and standardization of serological screening tests for coeliac disease in 1996. 3 rd EMRC/ESPGAN Workshop, Dec 5–8, 1996, Molsheim, France, pp:9–24; Catassi C et al. 1999. Quantitative anti-gliadin antibody measurement in clinical practice: an Italian multicenter study. Ital J Gastroenterol Hapatol 31; 366–370). AGA are mainly detected by ELISA, a more simple method than IF, and can be used for the analysis of large number of samples. Nevertheless AGA are less specific for CD than EMA and the detection of antibodies of IgA or IgG isotypes requires two independent assays. Recently a visual immunoassay for the detection of AGA, which solves some of these problems, has been reported (Garrote J A, Sorell L, Alfonso P et al 1999. A simple visual immunoassay for the screening of coleliac disease. Eur. J Clin Invest 29; 697–699; Spanish Office for Patents and Marks No. 9801067).

In 1997, Dietrich et al identified tissue transgluaminase (tTG), an 85 kDa protein, as the major, if not the sole, auto antigen detected by anti-endomysial antibodies (Dietrich W et al. 1997. Identification of tissue transglutaminase as the auto antigen of celiac disease. Nat Med. 3:797–801). Detection of anti-tTG antibodies had been reported lately in ELISA or radio-ligand (RLA) formats based on tTG from guinea pig liver extracts or recombinant human tTG cloned from different tissues (Sulkanen S et al. 1998. Tissue transglutaminase autoantibody enzyme-linked immunosorbent assay in detecting celiac disease. Gastroenterology 115:1322–1328; Siessler J et al. 1999. Antibodies to human recombinant tissue transglutaminase measured by radioligand assay: Evidence for high diagnostic sensitivity for celiac disease. Horm Metab Res 31; 375–379).

Anti-transglutaminase assays have shown a similar or better sensitivity and specificity for celiac disease diagnosis than EMA (Bazzigaluppi A et al. 1999. Comparison of tissue transglutaminase-specific antibody assays with established antibody measurement for coeliac disease. Journal of Autoimmunity 12:51–56; Amin M et al. 1999. Correlation between tissue transglutaminase antibodies and endomysium antibodies as diagnostic markers of coeliac disease. Clin Chim Acta 282: 219–225). As mentioned before, EMA assays was considered until now the best serological test for the diagnosis of CD.

Nevertheless the detection of anti TG antibodies by ELISA or RLA has some limitations. They are instrumental techniques that require and spectrophotometer or a radioactive-counter, a highly technical expertise, and are laborious and time consuming methods with multiple operations. Besides, two independent assays are required to detect IgG and IgA anti-TG antibodies.

Different immunochromatographic assays (ICA) have been developed for the diagnosis of pregnancy, and infectious and non infectious diseases. The general principles ICA are under intellectual property, among them, Shanfun Ching et al. EP 0 299 428 B1, Rosenstein R. EP 0 284 232 B1, which are related to the present invention.

Other patents claimed the utilization of these assays in the detection of different biomolecules (Campbell R. U.S. Pat. No. 4,703,017), drugs and non-protein antigens (Sung M. U.S. Pat. No. 5,238,652), and for tumor associated antigens (Manita Hideaki et al. EP 0396801).

The main purpose of the present invention is to develop a simple visual assay, for the detection of anti TG antibodies. This method easy to perform does not require any laboratory equipment and the results are reached in about 15 minutes by a one-step operation. The assay allows the detection in a simple test of IgG and IgA anti-TG antibodies in human blood, serum or plasma, by just putting the sample in the indicated place and waiting out for the result of the test. To our knowledge this method is the easiest and fastest assay yet developed to detect anti TG antibodies for celiac disease diagnosis The assay can be performed in laboratories with a minimal technical support, in physician's office, both in urban or rural areas, or even be used as an auto-test.

DETAILS OF THE INVENTION

According to the present invention a third generation immunochromatographic assay was developed to detect IgG and IgA anti-TG antibodies in just one-step in human blood, serum or plasma for celiac disease diagnosis.

The system has the following basic components (FIG. 1):

1. Antigen: Tisular transglutaminase (tTG), obtained from natural source or by recombinant DNA technology. The antigen conjugated to a colored substance, like colloidal gold or colored latex particles, serves as the tracer in the system
2. An inert porous support, where the conjugated antigen is deposited and dried. This support allows the release of the conjugated when it comes into contact with a liquid sample.
3. A nitrocellulose or nylon membrane with a pore size between 5 to 10 $\mu$m that allows the migration of the reactants as a lateral flow through the membrane.
4. The antigen (tTG) immobilized onto a "reactive zone" of the nitrocellulose or nylon membrane where it is firmly bound by electrostatic and hydrophobic interactions
5. A control reagent able to react with the conjugated antigen (for example, anti-TG antibodies, or a reagent able to bind colloidal gold), adsorbed onto the same membrane in a subsequent control zone, that serves to control the assay performance
6. An absorbent pad placed at the end, and in contact with, the membrane. The adsorbent pad allows the elimination of the excess of reagents after the migration.

In another embodiment, the invention provides a system for detecting celiac disease in a human. The system comprises (i) an inert porous support wherein tissue transglutaminase antigen conjugated to a colored substance is deposited and dried, and wherein the support allows release and laminar flow of the conjugated antigen when contacted with a liquid sample and (ii) a membrane comprising a reactive zone which comprises immobilized tissue transglutaminase antigen.

The principle of the test is based on the bivalence of human IgG and IgA molecules for the specific antigen. Based on this property it is possible that the same anti-TG antibody molecule reacts by one binding site with the antigen in solution, in this case tissue transglutaminase conjugated to the colored substance, while by the other binding site reacts with the fixed antigen onto the nitrocellulose or nylon membrane. This reaction is evident by forming a colored signal in the "reactive zone" of the membrane (FIG. 2).

In the practice, when a volume of 100 to 300 $\mu$L of a liquid sample is added to the conjugated antigen dried onto the inert support it is dissolved and migrates through the membrane. If the sample contains specific anti-TG antibodies they react with the labeled antigen developing an stable immuncomplex. Later, the immunocomplexes migrate to the "reactive zone" where they are captured by the same antigen (transglutaminase) fixed onto the membrane. The result of this reaction is a visible colored signal in the "reactive zone" as a result of the deposition of the labeled immunocomplexes in this place. In negative samples for the presence of anti TG antibodies, the immunocomplexe won't be developed, therefore no colored signal will be visible in the "reactive zone" of the membrane (FIG. 2).

To control the assay performance, a reagent which reacts with the conjugated antigen is adsorbed onto the same membrane in a subsequent "control zone" (FIG. 2). This way, a colored signal will be visible in the "control zone" in both, positive and negative samples (FIG. 2). This second colored signal serves to control the functionality of the test.

Finally, an adsorbent pad placed at the end of the membrane, and in contact with it, allows the elimination of the excess of reagents and improve the flow conditions (FIG. 1).

EXAMPLES

Example 1

Assay Method

Tissue transglutaminase obtained from natural source or by DNA recombinant technology is conjugated to colloidal gold particles (20 to 40 $\mu$m of diameter), according to Oliver C. (Oliver C, 1994. Conjugation of colloidal gold to proteins, Chapter 38 In: Javois LC, Human Press Inc., ed. Method Mol Biol, 34:303–307).

When a sample of serum, plasma or blood is added to the inert support where the conjugated is deposited, the specific anti-TG antibodies react with the conjugated antigen developing an immunocomplex (IC) that migrates through the nitrocellulose (NC) membrane (4 mm wide, 5–10 $\mu$m pore size). In a few minutes the IC reacts with the immobilized antigen (tTG) in the "reactive zone" of the NC forming a colored signal in this place. In negative samples without specific anti-TG antibodies, IC will not be developed and therefore no colored signal will be seen in the "reactive zone" of the NC.

Example 2

Control of the Assay Performance

For the evaluation of the assay performance, an anti-TG monoclonal antibody is adsorbed onto the same NC membrane in a subsequent "control zone", upper than the "reactive zone" regarding the sample application site. When the excess of conjugated antigen reaches this zone reacts with the monoclonal antibody given a colored signal.

According to the above two examples, the results of the test can be interpreted by visual examination of the reactive and control zones after 15 minutes of the sample application. The possible results are the following (FIG. 3):

Presence of two colored signals: Positive sample

Presence of only a colored signal in the "control zone": Negative sample

None colored signal Non-valid result. Repeat the test.

Advantage of the Method

1. Is a one-step test.
2. The assay does not require any instrumental equipment.
3. Easy to interpret the results.
4. Results in less than 15 minutes,
5. Detection of IgG and IgA anti TG antibodies in the same test.
6. Effective method for diagnosis of celiac disease in patients with deficit of IgA
7. The assay can be performed with serum, plasma or blood samples

Figure 1:
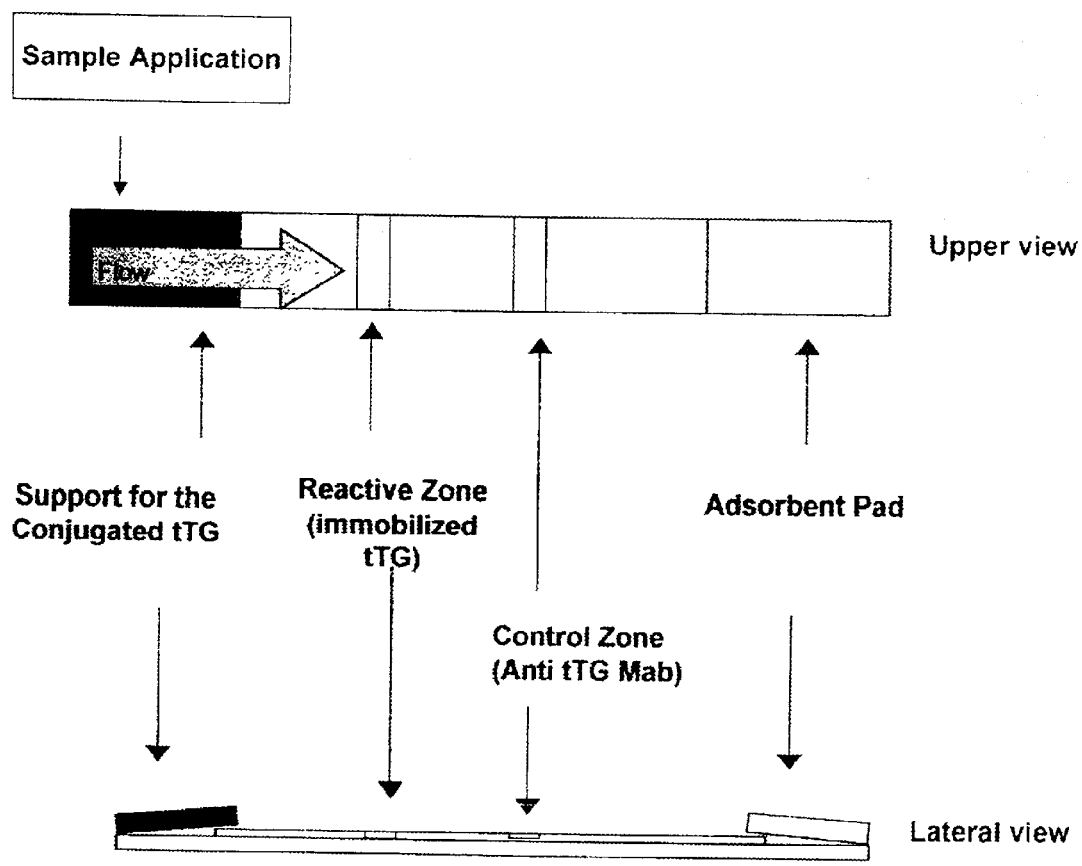
FIG. 1. General scheme of the assay. The conjugated antigen (tissue transglutaminase conjugated to a colored tracer) is dried onto an inert fibrous support. The same antigen (tissue transglutaminase) is adsorbed onto a "reactive zone" of a nitrocellulose or nylon membrane. A monoclonal anti-transglutaminase antibody is adsorbed onto the same membrane in a subsequent "control zone". At the end of the right side the absorbent pad that allows the elimination of the excess of reagents after migration. The wide arrow indicates the direction of the lateral flow. The zone for the sample application is also showed.
Figure 2:
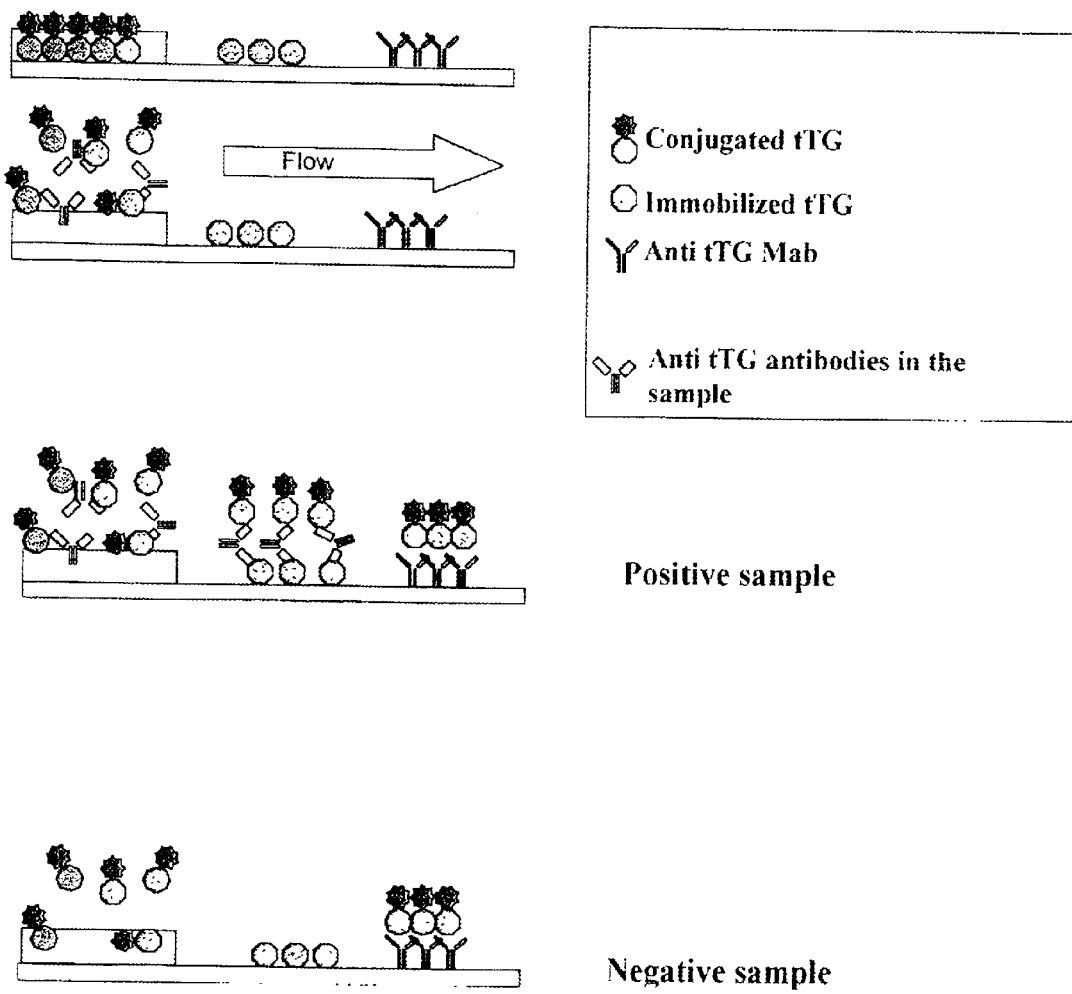
FIG. 2. Assay principle. When the conjugated support is dipped on a liquid sample anti tissue tranglutaminase antibodies react with the conjugated antigen, developing and immunocomplex that migrates through the membrane strip. Immobilized tissue transglutaminase in the nitrocellulose reacts with the immunocomplexes, because of the bivalence of antibodies molecules, forming a colored signal in the "reactive zone". Excess of conjugated antigen and immunocomplexes continue migration and finally react with the anti tTG monoclonal antibody forming a second colored signal in the strip. A positive result, indicating the presence of anti-tTG antibodies in the sample, will be seen as two subsequent visually detectable signals in the strip. A negative assay shows only a colored signal at the "control zone" because the immunocomplexes were not developed.
Figure 3:
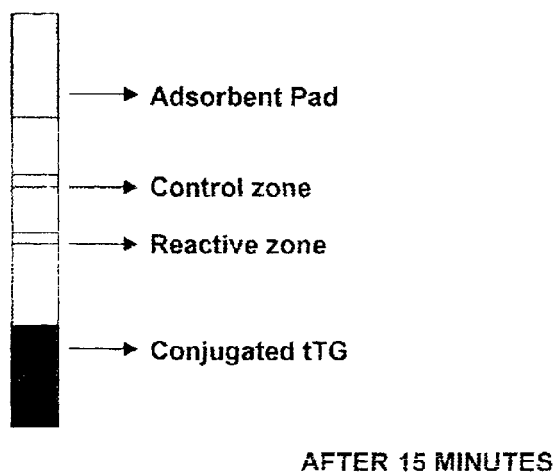
FIG. 3. Interpretation of the results. Fifteen minutes after the addition of the sample.
Figure 3:
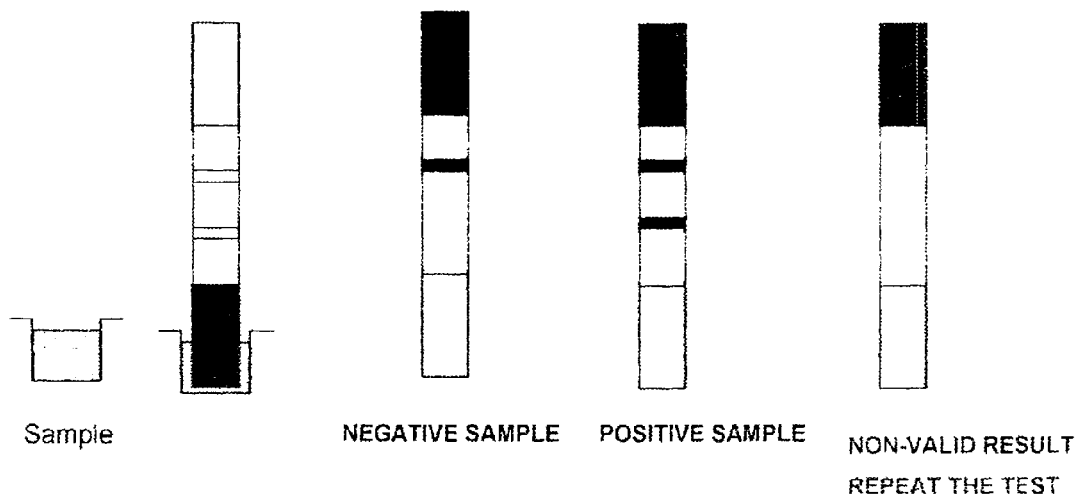

Only one colored signal in the control zone: indicates a negative result

Two colored signals: indicates a positive result

None colored signal: indicates a non-valid result, so that the assay should be repeated

What is claimed is:

1. A method for detecting IgA or IgG anti-transglutaminase antibodies in liquid samples, the method comprising:

a) providing a system comprising:
(i) an inert porous support wherein tissue transglutaminase antigen conjugated to a colored substance is deposited and dried, and wherein the support allows release and laminar flow of the conjugated antigen when contacted with a liquid sample; and
(ii) a membrane comprising a reactive zone which comprises immobilized tissue transglutaxninase antigen;

b) obtaining a liquid sample from a human;

c) adding the liquid sample to the inert porous support containing tissue transglutaminase antigen conjugated to a colored substance, wherein the conjugated antigen and/or immunocomplexes formed between antibodies in the sample and the conjugated antigen migrate to the reactive zone by laminar flow; and d) detecting any binding between the immunocomplexes formed in step c) with the immobilized antigen, wherein binding of the immunocomplexes with the immobilized antigen in the reactive zone indicates the presence of IgA or IgG anti-transglutaminase antibodies in the sample.

2. The method according to claim 1, wherein the membrane further comprises a control zone, wherein the control zone comprises a control reagent that binds with the conjugated antigen.

3. The method according to claim 2, wherein the method further comprises detecting binding of the conjugated antigen with the control reagent, wherein binding of the conjugated antigen with the control reagent indicates performance of the method.

4. The method according to claim 1, wherein the sample is blood.

5. The method according to claim 1, wherein the sample is plasma.

6. The method according to claim 1, wherein the sample is serum.

* * * * *